United States Patent [19]

Zuckerkandl

[11] Patent Number: 4,863,729

[45] Date of Patent: Sep. 5, 1989

[54] METHOD FOR PREPARING A MACROMOLECULAR MONOCLONAL ANTIBODY COMPOSITION

[75] Inventor: Emile Zuckerkandl, Palo Alto, Calif.

[73] Assignee: Linus Pauling Institute of Science and Medicine, Palo Alto, Calif.

[21] Appl. No.: 918,588

[22] Filed: Oct. 10, 1986

Related U.S. Application Data

[63] Continuation of Ser. No. 622,384, Jun. 20, 1984, abandoned, which is a continuation of Ser. No. 380,092, May 20, 1982, abandoned.

[51] Int. Cl.$^4$ .................. A61K 39/395; C07K 3/00; C07K 17/06; C07K 17/10
[52] U.S. Cl. .................. 424/85.8; 424/85.91; 424/78; 424/450; 530/387; 530/389; 530/390; 530/391; 530/402; 530/403; 530/404; 530/405; 530/813; 530/816; 530/817; 514/23; 514/54; 435/68; 435/69; 436/529; 436/532; 436/535; 436/829
[58] Field of Search ............. 530/387, 389–391, 530/808, 810, 816, 817, 813, 402–405; 424/78, 85, 450, 85.8, 85.91; 514/23, 54; 435/68, 69; 436/529, 532, 535, 829

[56] References Cited

U.S. PATENT DOCUMENTS

| | | | |
|---|---|---|---|
| 4,046,722 | 9/1977 | Rowland | 260/112 R |
| 4,172,124 | 10/1989 | Koprowski et al. | 424/85 |
| 4,273,865 | 6/1981 | Stetten et al. | 530/363 |
| 4,363,758 | 12/1982 | Masuho et al. | 424/85 |
| 4,673,734 | 6/1987 | Tayot et al. | 530/417 |
| 4,698,420 | 10/1987 | Urnowitz | 530/389 |

FOREIGN PATENT DOCUMENTS 82-01011  4/1982  World Int. Prop. O. ............ 424/85

OTHER PUBLICATIONS

Ho et al., *Biochemistry* 25, 1986, pp. 550–06.
Costello et al., Clin. Chem. 25(4) 1979, pp. 1572–1580.
Leserman et al., Targeting to Cells of Fluorescent Liposomes Covalently Coupled with Monoclonal Antibody or Protein A, Nature 288, 602–604.
Vogel et al., Induction of Immune Cytolysis, Proc. Natl. Acad. Sci. USA 78(12), 7707–7711 (Dec. 1981).
Dippold et al., Cell Surface Antigens of Human Malignant Melanoma, Proc Natl. Acad. Sci. U.S.A. 77(10), 6114–6118 (Oct. 1980).

*Primary Examiner*—Delbert R. Phillips
*Assistant Examiner*—Garnette D. Draper
*Attorney, Agent, or Firm*—Flehr, Hohbach, Test, Albritton & Herbert

[57] ABSTRACT

Macromolecular monoclonal antibody compositions are provided which are capable of selectively forming stable bonds to cells having a predetermined concentration of at least one surface antigen, such concentration being greater in such cells than in other cells in the cell population, wherein the composition comprises a substrate and a plurality of monoclonal antibodies specific to said surface antigen or antigens, which antibodies are covalently bonded to the substrate.

4 Claims, No Drawings

METHOD FOR PREPARING A MACROMOLECULAR MONOCLONAL ANTIBODY COMPOSITION

This is a continuation of application Ser. No. 622,384, filed June 20, 1984, now abandoned, which is a continuation of application Ser. No. 380,092, filed May 20, 1982, now abandoned.

The present invention is directed to a method for selectively marking particular cells within a cell population by use of a macromolecular monoclonal antibody composition comprising a predetermined number and type of antibody molecules such that the composition is quantitatively specific to cells having a predetermined concentration of at least one target surface antigen. The predetermined concentration of the target surface antigen is such that the concentration of the antigen is greater on the surface of the cells to be selected than in other cells in the cell population.

Among the uses for monoclonal antibodies, there are proposed methods of binding to specific antigen sites on selected cells. In particular, there are investigations in which monoclonal antibodies are used against malignant cells once the identity of cell surface antigens characteristic of the malignant cells are known. However, thus far the use of monoclonal antibodies in this way has not been generally satisfactory. Several reasons may be hypothesized to account for the unsatisfactory use of monoclonal antibodies in this respect. One reason may be that monoclonal antibodies may crossreact with unrelated proteins in other tissues having some structural portions in common with, or closely related to, the target antigen. Furthermore, some of the surface antigens thought to be characteristic only of malignant cells may also occur, to a lesser extent, in normal cells. Finally, normal cells may contain antigens which vary slightly in structure from those present on the malignant cells, but the structural differences may be so small so as to still enable a stable bond to be formed between the antibody and the normal cell surface antigen. For these reasons, the use of monoclonal antibodies against malignant cells may also be accompanied by attack of normal cells. Thus, the structural specificity of monoclonal antibodies is insufficient, in most cases, for obtaining the desired therapeutic effect without undesirable side effects.

The present invention imparts quantitative specificity to a macromolecular monoclonal antibody composition, whereby the composition will be stably bound to a target cell only when a particular antigen, or antigens, are present at a concentration greater than a preselected threshold value. By antigen concentration is meant the concentration which is measured in a substantially two dimensional space, namely on the surface of a cell membrane. Since the antibody-antigen binding will occur at the cell surface the concentration of any antigenic material within the cell need not be considered.

It is therefore an object of the present invention to provide a monoclonal antibody composition which achieves quantitative specificity thereby rendering said composition capable of selectively forming stable bonds with cells having at least one surface antigen in greater than a threshold concentration.

Other objects of the invention will become apparent from the following specification and claims.

In order to achieve quantitative specificity, the monoclonal antibody compositions of the present invention are prepared by forming a macromolecular unit. This macromolecular unit comprises a plurality of monoclonal antibody molecules, a substrate and one or more of the following: linkers, which are subunits by which the antibody molecule may be joined to the substrate; bridges, which are bifunctional cross-linking agents which may form bridges between antibody molecules; and toxins or other substances which may be incorporated into the macromolecular unit and which would be toxic to the cell to which the unit binds.

The monoclonal antibodies utilized in the present invention may be generated by known techniques. The antibodies may be any of the antibody isotypes, allotypes or idiotypes, such as IgM, IgG, IgA, IgE, etc. The particular antibody which will be utilized will depend on the particular antigen which is found to be present in greater than normal concentration on the target cells. For example, it is known that human malignant melanomas express some normal surface antigens in greater than normal concentration. See Dippold et al., Proc. Natl. Acad. Sci. USA, 77, 6114 (1980) and Yeh et al., Proc. Natl. Acad. Sci. USA, 76, 2927 (1979). In some cases it may be advantageous to utilize a plurality of different antibodies, each of which corresponds to a surface antigen present in the target cell in greater than normal concentration. For these cases, the macromolecular unit according to the present invention may comprise a mixture of monoclonal antibodies such that the corresponding concentrations of the various antigens on the cell surface to which the antibodies will bind will be reflected by the proportions of the different corresponding monoclonal antibodies in the macromolecular unit. The type and concentration of cell surface antigens in a particular cell population may be readily determined by conventional screening techniques by those of ordinary skill. See for example, Yeh et al., supra, and Herlyn et al., Proc. Natl. Acad. Sci. USA, 76, 1438 (1979).

Since a target antigen may form a particularly strong antigen-antibody bond so that only a single antigen-antibody bond would be necessary in order for the macromolecular unit to be stably bound to the target cell, the quantitative selectivity would be lost because the macromolecular unit would be in such a case essentially acting as a single antibody molecule. Therefore, in many cases it may be necessary to modulate the binding site of the antibody by a chemical reaction such that it would require a plurality of modulated antibodies to form a stable bond between the macromolecular unit and the target cell surface. Such modulation may be accomplished, for example, by methylation of a tyrosine or serine hydroxyl group near, but not within, the binding site of the antibody. The aim of such chemical modifications is to decrease the affinity of the individual antibody bonding site for the antigen without appreciably affecting the antibody specificity.

It is preferred that the macromolecular unit comprise a type of antibody such that it would require about three or four antibody-antigen bonds in order for the macromolecular unit to be bound to the target cell surface. It will be recognized that when antibodies such as divalent IgG are used only an even number of bonds may be formed. The number of antibody-antigen bonds, n, required to be formed in order to bind the macromolecular unit to the target cell surface will be dependent upon the affinity of the antigen for the particular antibody binding site. In practice, for a given monoclonal antibody, the lower limit of n necessary to distinguish the target cells from the remainder of the cell population may be readily determined by screening fractions of macromolecular units having different molecular weight for their activity against target cells.

In order for n number of antibody-antigen bonds to be formed, it is necessary that all of the antibody molecules be arranged on the polymeric substrate so that they may simultaneously react with antigens on a cell surface. This requirement may be met by bonding the antibodies to a flexible substrate so that the antibodies are sufficiently flexible in their orientation to permit a plurality of antibody binding sites to simultaneously combine with antigens on a cell surface. The requirement may also be met by a polymeric substrate which is substantially planar so that all of the antibodies may be unidirectionally extending from the surface thereof.

The substrates to be utilized according to the present invention which anchor the antibody molecules may be polymeric substances such as polysaccharides, or liposomes.

The polysaccharides may be polydextrans, polyglucosides, etc. The polymeric substrate should be partially digestible by enzymes so that macromolecular units may be formed of a size which may be transported through the organism to the target cells. In the case of polysaccharides, many satisfactory enzymes are available such as dextranases, amylases, cellulases, etc. The polymeric substrate should be nonantigenic or not significantly antigenic in the host organism or culture.

The macromolecular unit may also be formed by cross-linking antibody molecules with other organic molecules, such as non-antigenic proteins and polypeptides, with conventional bifunctional cross-linking agents. The macromolecular units may be formed by reacting antibody molecules and organic molecules in the presence of bifunctional reagents. In such cases, the polymer comprises the cross-linked antibodies and other molecules. Such organic molecules may be toxins or cytotoxic drugs which would cause the target cell to die.

The antibodies may also be covalently bonded to liposome surfaces according to the method of Leserman et al., Nature, 293, 226 (1981), the disclosure of which is incorporated herein by reference. Monoclonal antibodies covalently bonded to liposomes carrying cytotoxic drugs, may be delivered into target cells, to eradicate the cells. While the mechanism of binding and ingesting the liposome bound antibodies is not clear, it is believed that the initial binding or non-binding mechanism which would determine whether the target cell is attached, is dependent upon the threshold concentration of the surface antigen or antigens which differentiate the target cells from the rest of the cell population. The use of liposomes is thus an alternative to the covalent linking of a toxin, such as the ricin A-chain, to an antibody molecule or polymeric substrate.

In forming the macromolecular units according to the present invention, it is not necessary that the entire antibody molecule be utilized. Only the portion containing the antigen binding site is required and extraneous portions of the antibody molecule may be omitted. Various peptidases may be utilized to cleave the antibody protein and conventional techniques may be utilized to isolate the fraction containing the antigen binding site.

The chemistry for either directly forming covalent bonds between the antibody or antibody fragment and substrate, or between the antibody, linker and substrate, respectively, is well known. See for example the reagents and procedures described in A. N. Glazer, *The Proteins,* Vol. IIA, 3rd Ed., and Neurath and R. L. Hill, Editors, Academic Press, pp. 1-103 (1976); and A. N. Glazer et al., "Chemical Modification of Proteins", *Laboratory Techniques in Biochemistry and Molecular Biology,* Vol. IV, Part I, T. S. Work and E. Work, Editors, North-Holland Publishing Company (1975); and K. Peters et al., *Ann. Rev. Biochem.,* 46, 423-51 (1977), the descriptions of which are incorporated herein by reference. Further examples of commercially available linking agents are disclosed in the Pierce 1981-82 Handbook and General Catalogue, pp. 161-166, Pierce Chemical Company, Rockford, Ill. Known linking procedures as described in the above publications may be employed. For example, the monoclonal antibody peptide may be reacted with iminothiolane, thereby placing an accessible sulfhydryl group thereon. The substrate or other linker protein may be activated by a reaction with succinimidylpyridylthiopropionate. The mixture of these two prepared components would result in joining thereof through dsulfide bonds.

The macromolecular units according to the present invention may be utilized according to known methods for introducing monoclonal antibodies to cell culture or for administering monoclonal antibodies in mammals. See, for example, Levy et al., *New Eng. J. Med.,* 306, 517 (1982). If administered to mammals, such as mice, rats, rabbits or guinea pigs, the monoclonal antibody composition may be administered subcutaneously, intramuscularly, intravenously, intraperitoncally, or otherwise, depending upon the most efficacious way of reaching the target cells. The dose of the macromolecular unit which is administered or introduced will depend on the mass, location and distribution of the target cells within one mammal or culture. Exemplary techniques utilized for use of monoclonal antibodies in humans, animals, and cell cultures are described by Levy et al., supra, Young et al., Science, 211, 487 (1981), and Yeh et al., supra, respectively, the disclosures of which are incorporated by reference herein.

Another approach in utilization of the quantitative specificity according to the present invention is to form a collection of various monoclonal antibodies to be generated against various antigens which occur on the surfaces of fetal cells. From this collection those antibodies which will react with non-target adult cells are to be eliminated. The residual monoclonal antibodies are to be utilized to react with target adult cells. Antibodies identified in this second reaction are retained and utilized to form the macromolecular units according to the present invention. The approach of this method is based on the theory that fetal cells may contain antigens which are most generally present in malignant target cells from the adult and which are most generally absent from non-target adult cells.

The macromolecular units prepared according to the present invention for achieving quantitative specificity of antibodies may be utilized for marking, for purposes of isolation, various types of cells which may be finely divided in terms of their state of differentiation of physiological state when these states may be characterized by absolute quantities of a given antigen or mixture of antigens on the cell surface. The cell isolation technique may be utilized, for example, in the following way. It is known that in certain types of cells the phenomenon of capping occurs, i.e., the congregation in one area of the cell surface of most of the antigen molecules. Thus if capped cells are to be isolated the macromolecular unit according to the present invention will react with that capped area of the cell surface, thereby targeting the cell for destruction or isolation.

The macromolecular units may be utilized in the area of curative medicine. For example, they may be used for the control of allergy or for eradicating malignant cells. For example allergy causing antibodies are produced by IgE secreting cells of the B lymphocyte type. These IgE secreting cells may not have on their surfaces any antigens that distinguish them sufficiently from cells which produce other antibody isotypes, therefore ordinary monoclonal antibodies made against IgE or against other antigens present on the surface of IgE producing cells may crossreact with other B cells as well as with other different types of cells. If, however, a macromolecular unit exhibiting quantitative specificity is formed against one or several antigens present on the surface of IgE producing B cells, these cells may be singled out with a degree of specificity not achievable heretofore. Destruction of these cells may reduce the IgE secretion and eliminate the allergic effects.

The quantitatively specific macromolecular units may also be useful in diagnostic medicine. In particular, diagnosis in the central nervous system has proven to be heretofore difficult. The central nervous system contains cells with fine, yet important differences from one another. It is believed that there has been heretofore unavailable an effective means for sorting such fine differences especially, in situ, in living organisms. However, the quantitatively specific macromolecular units may be used for selective treatment of cells in the central nervous system, and in other anatomical locations, which may be identified with a high degree of specificity.

There are other areas in which isolation and/or identification of specific cell types are important. For example in the field of diagnosis, the macromolecular units may be used as imaging vectors. Imaging may be attained by binding the macromolecular units to an appropriate molecular payload.

Chemical microsurgery may be accomplished by attaching a cytotoxic payload to the macromolecular unit and allowing the unit to seek and selectively kill stringently defined subtypes of cells in the central nervous system or elsewhere in the organism. Finally, the use of quantitative selectivity has apparent uses in biological and molecular biological research, particularly in the investigation of cell development, differentiation and activation. For example, it is known that glycoprotein 70 is expressed in activated mouse lymphocytes, but may be found in lesser amounts on other cells. Klenner et al., Proc. Natl. Acad. Sci. USA, 79, 1250 (1982). This observation therefore may be a basis for identifying activated cells by macromolecular units comprising monoclonal antibodies which complement glycoprotein 70. Also differences in antigenic specificity among cell types and subtypes in the central nervous system have been reported. See Sternberger et al., Proc. Natl. Acad. Sci. USA, 79, 1326 (1982). The macromolecular units may thus be utilized to isolate and/or kill selectively finely defined subtypes which are present during development and differentiation stages of the organism and which would be beneficial to gaining new insights into such cell mechanisms.

The following examples are presented to illustrate the present invention, however the invention is not deemed to be limited to the particular embodiments set forth.

EXAMPLE 1

Spleen lymphocytes obtained from mice immunized against human melanoma cell line and melanoma-mouse hybrid cells are fused with the P3x63 Ag8 mouse myeloma according to procedures described by Koprowski et al., Proc. Natl. Acad. Sci. USA, 75, 3405 (1978), to produce hybrids secreting monoclonal antibodies against a human melanoma. Among the twenty-nine hybrid cultures obtained, nine show the presence of antimelanoma antibody. Among these nine cultures, two (691-2, 691-12) react with all (six total) melanomas used by screening activity, four out of the five colorectal carcinomas and all three of the normal human cultures.

Antibodies from the cultures 691-2 and 691-12 are respectively isolated from the culture medium (see Jensenius et al., Eur. J. Immunol, 4, 91 (1974)), treated with iminothiolane, and covalently linked to dextran activated with succininidylpyridylthiopropionate. The substrate bound antibodies are then treated with dimethyl sulfate to modulate the binding potential of the antigenic binding sites. The dextran substrate is then partially degraded by digestion with dextranase and the fractions according to molecular weight. At least one fraction of the substrate bound 691-2 and 691-12 monoclonal antibody, respectively, will react with one or more of the melanomas or colorectal carcinomas used previously, and will not react with any of the three normal human cultures.

EXAMPLE 2

Monoclonal antibody IgG is linked to dextran. The substrate is then degraded enzymatically by dextranase according to known techniques to block progressive degradation. Soluble fragments will be obtained carrying different numbers of antibody molecules and fractions may be separated by molecular weight according to known techniques such as electrophoresis, chromatography, etc. The procedure may be illustrated as follows, wherein Ab indicates a monoclonal antibody molecule:

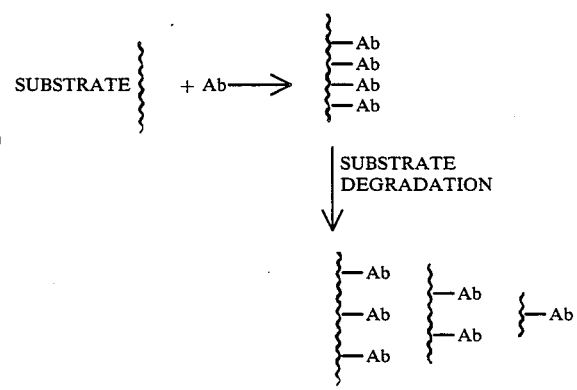

EXAMPLE 3

Monoclonal antibody molecules are cross linked with the bifunctional linker dipyridylsulfide. The fraction containing the desired number of n antibody molecules and physical properties may be separated according to conventional techniques. This scheme is illustrated below:

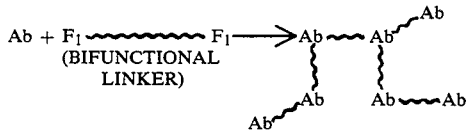

A mixture of monoclonal antibodies and the protein toxin ricin A-chain may be reacted with a bifunctional cross-linker such as dialdehyde or diimidoether according to known techniques. See Krolick et al., Proc. Natl. Acad. Sci. USA, 77, 5419 (1980). This produces a macromolecular structure comprising cross-linked antibody and toxin molecules. This macromolecular structure is then separated into fractions to isolate the macromolecular unit containing the desired number of n antibody units. This scheme is illustrated below:

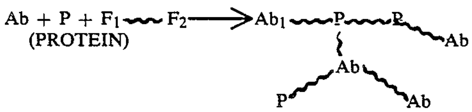

EXAMPLE 4

The procedure described above in Example 2 is modified by directly bonding the antibody and/or toxin protein to a low molecular weight water-soluble polymer carrying functional groups capable of reacting with functional groups present on the antibody and toxin protein. Such polymers may be, for example, polyacrylates, polyanhydrides, polyaldehydes, polysaccharides, etc. The resultant macromolecular units will contain antibody molecules and toxin molecules directly bonded to the substrate and may be fractionated according to conventional methods to isolate the particular desired structure having the required number of antibody units. These methods are illustrated by the following scheme:

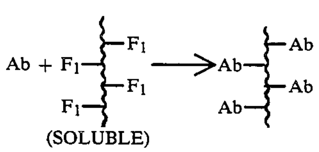

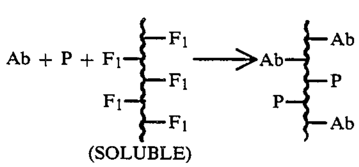

EXAMPLE 5

The procedures given above in Examples 2, 3 and 4 may be modified for use of a mixture of monoclonal antibodies. For example, in a case where the macromolecular unit is required to have two different antibodies, antibody 1 and antibody 2, linking agents will be chosen having functional groups $F_1$ and $F_2$, or low molecular weight polymeric substrates will be chose having functional groups $F_1$ $F_2$, such that one of the $F_1$ or $F_2$ groups will react only with antibody 1. The other $F_1$ or $F_2$ group will react with any common functional group present in a protein, such as $HN_2$. Therefore, by sequential reactions with antibody 1 and antibody 2 separated by a fractionation step, the desired macromolecular unit having the desired antibody 1 and antibody 2 ratios, $(antibody_1)_m$ $(antibody_2)_n$ may be isolated. These schemes are illustrated below:

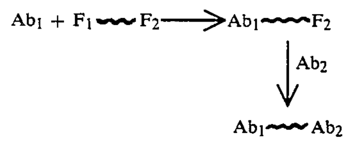

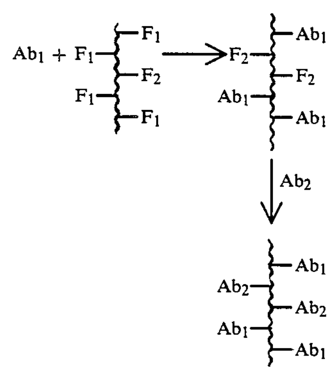

EXAMPLE 6

In some cases the antibody or antibodies which are utilized may be partly inactivated by utilizing the conventional chemical procedures described above in Examples 1 through 4. In such a case if partial inactivation is not desired the respective antibody binding sites may be protected by first reacting the antibody with its corresponding antigen, thereby protecting the antibody binding site. The bound antibody may then be functionized with a linker group in a heterogeneous phase containing the bound antibody, followed by release of the antibody from the antigen to yield an antibody functionalized with a linker group. These methods are illustrated below, wherein Ag is an antigen molecule:

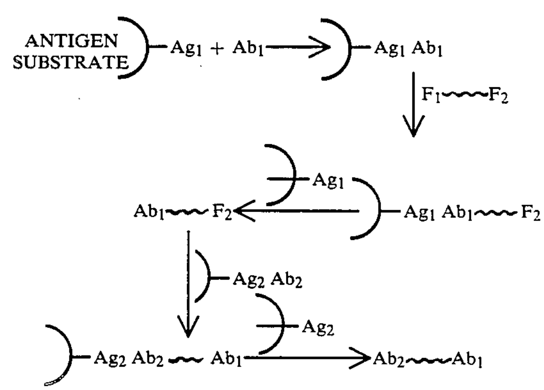

The cross-linked antibody moiety, $Ab_2Ab_1$, may then be treated according to any of the procedures described in the previous examples.

What is claimed is:

1. A method of making a macromolecular monoclonal antibody composition capable of selectively forming stable bonds to cells having at least a predetermined threshold concentration of at least one surface antigen, comprising the steps of:
(1) forming covalent bonds between a plurality of monoclonal antibodies and a substrate selected from the group consisting of polysaccharides and liposomes; and
(2) enzymatically cleaving said substrate to form said macromolecular antibody composition.

2. A method of preparation of a macromolecular monoclonal antibody composition capable of selectively forming stable bonds to cells having at least a predetermined threshold concentration of at least one surface antigen, comprising the steps of forming covalent bonds between said antibodies and a substrate selected from the group consisting of polysaccharides and liposomes, said substrate characterized as being water soluble and having functional groups capable of reacting with functional groups present on said antibodies; and separating the fraction containing said macromolecular monoclonal antibody composition having a number of antibodies bound to each substrate molecule capable of selectively forming stable bonds to cells having a said predetermined concentration of at least one surface antigen.

3. The method according to claim 2 further comprising the step of forming covalent bonds between said substrate and a toxic substance capable of killing a cell when said cell is bound to said macromolecular monoclonal antibody composition.

4. The method according to claim 1 or 2 wherein said monoclonal antibodies comprise a mixture of at least two different antibody types.

* * * * *